(12) United States Patent
Cordani et al.

(10) Patent No.: US 7,182,778 B2
(45) Date of Patent: Feb. 27, 2007

(54) CONFORMING THERMAL PACK

(75) Inventors: Peter J. Cordani, Palm Beach Gardens, FL (US); Lawrence J. Dutton, Port St. Lucie, FL (US); Anne Cordani, Palm Beach Gardens, FL (US)

(73) Assignee: Gel Tech Solutions, Inc., Jupiter, FL (US)

( * ) Notice: Subject to any disclaimer, the term of this patent is extended or adjusted under 35 U.S.C. 154(b) by 728 days.

(21) Appl. No.: 10/001,047

(22) Filed: Nov. 1, 2001

(65) Prior Publication Data

US 2003/0083722 A1    May 1, 2003

(51) Int. Cl.
*A61F 7/02* (2006.01)
*A61F 7/00* (2006.01)

(52) U.S. Cl. .................... 607/114; 607/108

(58) Field of Classification Search .......... 607/96, 607/108–114; 126/263, 263.01, 263.02, 126/263.03, 263.04, 263.05, 263.06, 263.07, 126/263.08, 263.09, 263.1; 62/4
See application file for complete search history.

(56) References Cited

U.S. PATENT DOCUMENTS

| | | | |
|---|---|---|---|
| 4,106,478 A * | 8/1978 | Higashijima | 149/15 |
| 4,203,445 A | 5/1980 | Jessup et al. | |
| 4,856,651 A * | 8/1989 | Francis, Jr. | 206/219 |
| 4,953,550 A | 9/1990 | Dunshee | |
| 5,171,439 A | 12/1992 | Vakharia | |
| 5,205,278 A * | 4/1993 | Wang | 126/263.03 |
| 5,261,532 A * | 11/1993 | Fauci | 206/218 |
| 5,456,704 A * | 10/1995 | Kilcullen | 607/111 |
| 5,534,020 A * | 7/1996 | Cheney et al. | 607/108 |
| 5,558,255 A * | 9/1996 | Sancoff et al. | 222/189.06 |
| 5,839,582 A * | 11/1998 | Strong et al. | 206/524.8 |
| 6,248,125 B1 | 6/2001 | Helming | |
| 6,264,681 B1 * | 7/2001 | Usui | 607/111 |
| 6,293,394 B1 * | 9/2001 | Marbler et al. | 206/218 |
| 6,318,359 B1 * | 11/2001 | Schmidt et al. | 126/263.03 |

* cited by examiner

Primary Examiner—Henry M Johnson, III
(74) Attorney, Agent, or Firm—McHale & Slavin PA

(57) ABSTRACT

A flexible thermal pack to be intimately applied to a patient's body is in the form of a plastic container enclosing a chemical compound capable of an endo- or exo-thermic reaction when intermixed with a catalyst. The plastic container has a vent in one wall covered by a semipermeable membrane for passage of gas but not liquid. Also enclosed in the container is another frangible container housing a suitable catalyst for the compound.

9 Claims, 3 Drawing Sheets

CONFORMING THERMAL PACK

FIELD OF THE INVENTION

This invention relates to the medical field and patient care, specifically to thermal dressings intimately conforming to the shape of the patient's body. For the purposes of this disclosure, heat and cold refer to temperatures above and below the normal body temperature, respectively.

BACKGROUND OF THE INVENTION

The medical use of thermal therapy, both hot and cold, is well known to treat various maladies and traumas. Usually, application of heat is used stimulate the body to increase blood flow in an area in order to dissipate the heat build-up. This acts to prevent stiffness in a traumatized joint or appendage. The application of a cold pack reduces swelling and lessens perceived pain. Both of these standard treatments have a place in caring for a patient.

In a hospital or office, thermal appliances may be in stock to apply to various portions of the anatomy. However, in emergency medical services where space and/or weight may be limited, hot and cold treatment is generally restricted to simple containers or absorbent pads, having the desired temperature, applied directly to the affected part of the patient's body. Because of the infinite sizes and shapes of the body, the few thermal devices available do not always conform to the patient in such a way to provide the most effective treatment. To alleviate this problem, small thermal packs have been developed.

To eliminate the problem of maintaining both hot and cold packs at a predetermined temperature for prolonged periods of time, the use of pliant containers enclosing ingredients which, when combined, create an endo- or exo-thermic reaction are used to apply cold or heat to the desired location on the body. However, a by-product of these endo- or exo-thermic reactions is gas. The gas becomes trapped in the container rendering the thermal pack rigid and lacking in the ability to conform to the anatomy. In the extreme, the container may rupture putting the reacting chemicals in direct contact with the patient's body.

DESCRIPTION OF THE PRIOR ART

U.S. Pat. No. 6,248,125 issued to Helming discloses a thermal pack for treating the perineal and rectal area with either heat or cold. Both the hot pack and the cold pack have an envelope within which are two separate compartments housing ingredients that cause a thermal reaction when mixed together. To use the device the compartments are ruptured allowing the components to mix. There is no indication of any provision for the volume of ensuing gas that is created inside the fixed volume of the container.

Dunshee, U.S. Pat. No. 4,953,550, discloses a chemical thermal pack with two compartments and separated ingredients which will create an exo- or endo-thermal reaction when mixed. A portion of the outer container has a wall with capillary tubes formed there-through. The capillary tubes allow for the drainage of water from the interior of the pack. Additionally, the capillaries act as an insulator to prolong the effects of either the hot or cold pack.

Vakharia and Jessup et al, U.S. Pat. No. 5,171,439 and U.S. Pat. No. 4,203,445, respectively, disclose gas vents for plastic bags. The vents permit gases to migrate into or out of the bags to equalize pressure while preventing liquid from escaping.

What is needed in the art is a hot or cold pack that allows gas to escape and remains compliant after the initiation of the endo- or exo-thermic reaction so that it can conform intimately with the injured portion of the body.

SUMMARY OF THE INVENTION

Accordingly, it is an objective of the instant invention to teach a medical device to apply heat or cold to a patient by intimately conforming to the anatomy.

It is a further objective of the instant invention to teach a medical device that creates a thermic reaction within a compliant container by mixing two or more chemical compounds.

It is yet another objective of the instant invention to teach a medical device having a vented container which allows escape of gaseous by-products of a thermic reaction and remains compliant during use.

It is a still further objective of the invention teach a medical device with a vented compliant container which has two compartments separated by a frangible partition with each compartment enclosing an ingredient necessary to create a thermic reaction. By applying pressure to the container, the partition is ruptured allowing the ingredients to mix within the container producing a temperature change, a liquid or gel residue and gases. The gases pass through the vent to the atmosphere.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

Figure 1:
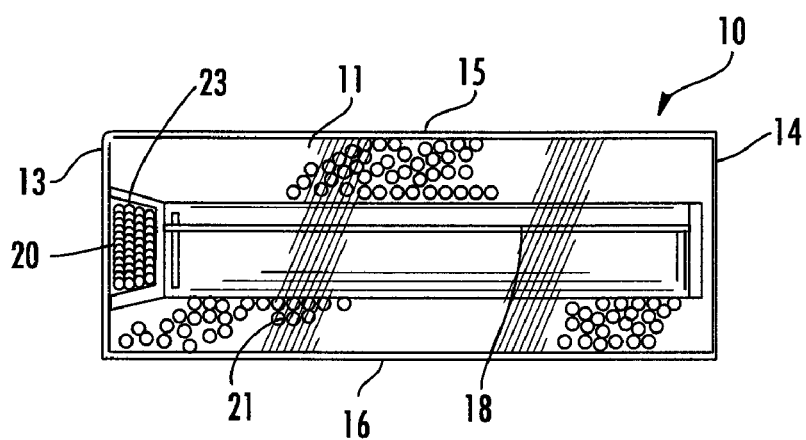
FIG. 1 shows a perspective of the thermal pack of the invention.

The thermal pack 10, shown in FIG. 1, is a generally rectangular container. The container may be made in different shapes as a matter of choice and for special applications. The container 10 is made of supple plastic films forming walls 11 and 12 which have seals 13, 14, 15 and 16 closing the corresponding edges to form a liquid tight container. The films may be single ply or co-extrusions of different polymers or laminated films having the same properties or different properties. The walls are formed of materials that will be impervious to each of the ingredients and to the resulting combination. The container may be made using a tubular plastic film which is sealed at the opposite ends. The plastic film may be thermoplastic and the seals may be formed by heat and pressure. If other plastic films are used, the seals may be formed by adhesives or solvents. As illustrated, the container 10 encloses, as one ingredient, a chemical compound 21 which will initiate a thermal reaction when mixed with another ingredient, in the form of a catalyst. Preferably, when the chemical compound is mixed with the catalyst a gel-like substance is formed. The gel acts to prolong the thermal effects.

Figure 2:
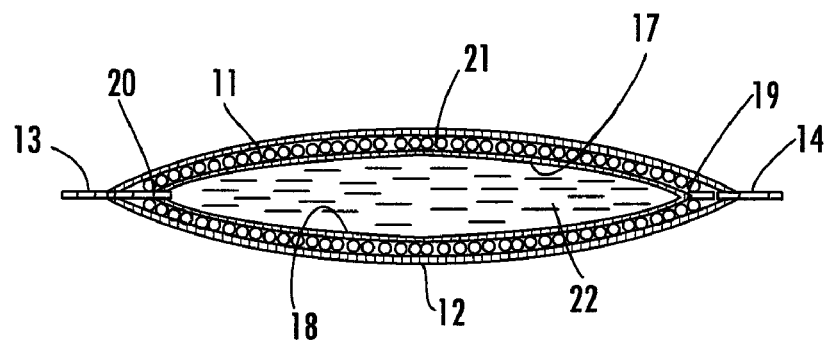
FIG. 2 shows a cross section of the thermal pack of FIG. 1 including separate compartments.
Figure 3:
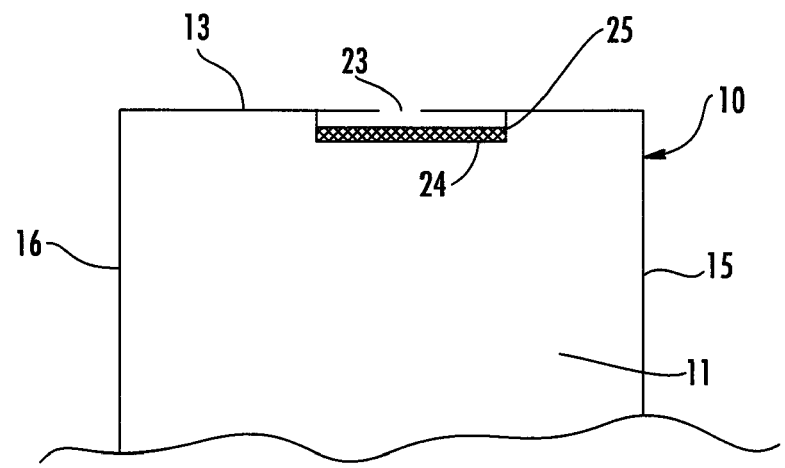
FIG. 3 shows a schematic cross section of the vent.

As shown in FIGS. 1 and 2, the container 10 encloses another tube having opposing walls 17 and 18. The walls 17 and 18 are preferably continuous plastic film with end seals 19 and 20. These films and seals may be formed in the same manner as the films and seals in container 10. Also, the tube may be formed by superimposing film layers and sealing the superposed periphery. The opposing walls 17 and 18 have a structure or are made of material that will rupture before the container 10, when placed under a compressive load. This insures the integrity of the container 10 and prevents the thermal compound from coming into contact with the user.

The catalyst 22, for the thermal reaction, is enclosed within the inner container until the inner container is ruptured. Once the thermal compound and catalyst come into contact with each other, the outer container is kneaded to thoroughly mix the ingredients.

As the thermal reaction progresses, there is generated a gaseous by-product. The volume of the gas is released from the interior of the container through aperture 23 and porous membrane 24. The porous membrane is made from a material that will allow passage of gas, including any air trapped in the interior, but not liquid. The membrane spans the aperture 23 and has a continuous edge seal 25 joining the membrane to the container. The edge seal 25 may be formed by heat and pressure, solvent or adhesives. The material of the membrane may be in the nature of a semipermeable membrane or it can be a microporous nonwoven material.

Figure 4:
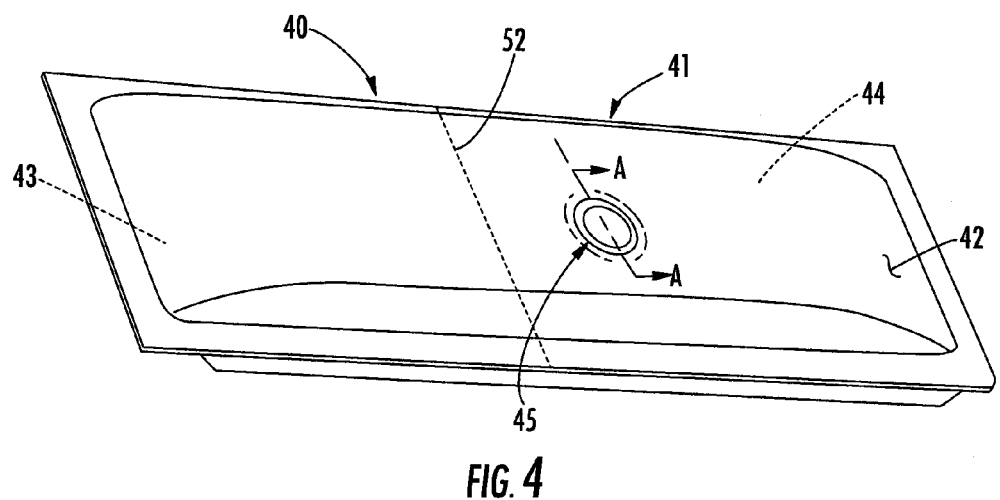
FIG. 4 shows a perspective of another embodiment of the thermal pack.

The thermal pack 40, shown in FIG. 4, is substantially similar to the thermal pack 10 of FIG. 1. The thermal pack 40 has a peripheral seal 41 and encloses a catalyst 43 inside the bag, separated from the thermal composition 44 by a frangible wall 52.

The thermal pack has a manual one-way valve 45 which has an annular valve 48 on the internal end of a valve body that reciprocates through a collar 46 sealed into an aperture in the thermal pack wall 42. The annular valve is seated into an annular recess 49.

Figure 5:
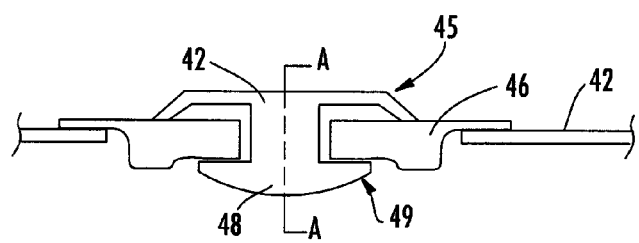
FIG. 5 shows a cross section of the closed vent valve along line A—A of FIG. 4.
Figure 6:
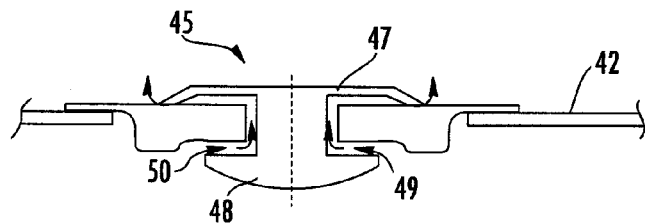
FIG. 6 shows a cross section of the open vent valve.

As shown in FIG. 5, the gas by-product of the thermal reaction caused by mixing the catalyst and the thermal composition will act against the annular valve 48 to seat the valve in the recess 49 closing the valve. The gas pressure closing the valve may be overcome by manually depressing valve actuator 47. The valve body moves displacing the annular valve 48 and opening a vent passageway 50. The gaseous by-product and any other trapped gases are released through the passageway.

As an example of the thermal pack, the outer container may be fabricated from polyethylene film, alone, or laminated with other materials, the thermal compound may be ammonium nitrate, either alone or mixed with other chemicals, disposed inside the outer container. The ammonium nitrate is in the form of dry particles.

The inner container may be made of the same plastic composition as the outer container. The inner container may have a weakened portion of a wall or the container may be of a thinner film. The catalyst, enclosed in the inner container, is water.

The vent may be a hydrophobic microporous nonwoven plastic material such as TYVEK made by DuPont Co. The vent material will allow gas to pass through while repelling liquid.

In use, the thermal pack may be stored indefinitely until the ingredients are mixed. To provide a cold treatment to a patient, the compliant envelope is squeezed or put under compressive pressure to rupture the inner tube. The container is then kneaded to thoroughly mix the chemicals and produce a temperature change. As the chemical endothermic reaction proceeds, gas evolves and escapes from the container through the semipermeable vent leaving the gel. The cold compliant container is then intimately wrapped about the injured part of the patient's body.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

What is claimed is:

1. A medical device for applying thermal treatment to the body by a chemical reaction comprising a pliant impervious container, said container enclosing an interior space, said container having an aperture there-through, said aperture defined by a continuous edge, and consisting of a single hydrophobic membrane spanning said aperture and sealed to said edge, said membrane adapted to pass gas but block liquid, a first ingredient in said interior space, a second ingredient in said interior space, a partition in said interior space separating said first and second ingredients, said partition adapted to be ruptured to mix said first and second ingredients, said first and second ingredients adapted to produce a thermal reaction resulting in the production of a thermal substance and gas, said gas exiting said interior space through said membrane whereby said thermal container may be conformed to the body.

2. A medical device of claim 1 wherein said thermal substance is a liquid.

3. A medical device of claim 1 wherein said thermal substance is a gel.

4. A medical device of claim 1 wherein said partition is an envelope containing one of said first or second ingredients, said envelope having walls formed of a plastic film, said walls adapted to rupture in response to compression.

5. A medical device of claim 4 wherein said first ingredient is water.

6. A medical device of claim 5 wherein said second ingredient is a chemical compound that produces an endothermic reaction when mixed with water.

7. A medical device of claim 6 wherein said chemical compound includes ammonium nitrate.

8. A medical device for applying a compliant thermal pack to a patient comprising a first container with compliant walls having a peripheral seal forming an interior space, a dry particulate chemical compound including ammonium nitrate disposed in said interior space, an aperture in one wall of said first container, said aperture having a continuous edge, and consisting of a semipermeable membrane closing said aperture and sealed about said continuous edge of said aperture, said membrane adapted to vent said first container of gases while blocking passage of liquid, a second impervious container in said interior space, said second impervious container housing a catalyst for said chemical compound adapted to intermix with said chemical compound to produce an endothermic chemical reaction resulting in the evolution of gas and a cold liquid, said second container adapted to rupture under a compressive force less than that required to rupture said first container, whereby when sufficient compressive force is applied to said first container said second container is ruptured intermixing said catalyst and said chemical compound resulting in an endothermic reaction with evolved gas passing through said semipermeable membrane leaving said cold liquid within said first container for intimate contact with a patient's body.

9. A compliant thermal pack for treatment of a patient comprising a sealed container having flexible walls, said container enclosing a thermal composition and a catalyst, said container having a frangible partition separating said thermal composition and said catalyst, said thermal composition adapted to produce an endothermic reaction and a gaseous by-product when mixed with said catalyst, a one-way valve reciprocatably mounted within said flexible walls, said one-way valve constructed and arranged to reciprocate from a closed position wherein the formation of said gaseous by-product act against said valve, and an open position wherein said valve is manually depressed to provide a vent for said gases whereby said container may conform to the patient.

* * * * *